(12) United States Patent
Qiu

(10) Patent No.: US 9,611,299 B2
(45) Date of Patent: Apr. 4, 2017

(54) METHOD FOR HIGHLY EXPRESSING RECOMBINANT PROTEIN OF ENGINEERING BACTERIA AND USE THEREOF

(71) Applicant: PROTEIN DESIGN LAB, LTD., Beijing (CN)

(72) Inventor: Xiaoqing Qiu, Beijing (CN)

(73) Assignee: Protein Design Lab, Ltd., Beijing (CN)

( * ) Notice: Subject to any disclaimer, the term of this patent is extended or adjusted under 35 U.S.C. 154(b) by 67 days.

(21) Appl. No.: 14/360,599

(22) PCT Filed: Nov. 23, 2012

(86) PCT No.: PCT/CN2012/085182
§ 371 (c)(1),
(2) Date: May 23, 2014

(87) PCT Pub. No.: WO2013/075660
PCT Pub. Date: May 30, 2013

(65) Prior Publication Data
US 2014/0322754 A1 Oct. 30, 2014

(30) Foreign Application Priority Data

Nov. 25, 2011 (CN) .......................... 2011 1 0380864

(51) Int. Cl.
| | | |
|---|---|---|
| C12N 15/62 | (2006.01) | |
| C07K 19/00 | (2006.01) | |
| C07K 14/00 | (2006.01) | |
| C12N 15/70 | (2006.01) | |
| C07K 14/245 | (2006.01) | |
| C07K 14/31 | (2006.01) | |
| C12P 21/02 | (2006.01) | |
| C12N 1/20 | (2006.01) | |

(52) U.S. Cl.
CPC .......... *C07K 14/001* (2013.01); *C07K 14/245* (2013.01); *C07K 14/31* (2013.01); *C12N 1/20* (2013.01); *C12N 15/62* (2013.01); *C12N 15/70* (2013.01); *C12P 21/02* (2013.01); *C07K 2319/01* (2013.01); *C07K 2319/035* (2013.01)

(58) Field of Classification Search
None
See application file for complete search history.

(56) References Cited

U.S. PATENT DOCUMENTS

| 8,563,503 | B2 | 10/2013 | Qiu |
| 9,073,989 | B2 | 7/2015 | Qiu |
| 2004/0058415 | A1 | 3/2004 | Tirrell et al. |
| 2012/0190826 | A1 | 7/2012 | Qiu |
| 2012/0202734 | A1 | 8/2012 | Qiu |

FOREIGN PATENT DOCUMENTS

| CN | 100999553 | 7/2007 | |
| CN | 200910157564.5 | 7/2009 | |
| CN | 200910092128.4 | 9/2009 | |
| CN | 101633699 | * 1/2010 | ............ C07K 19/00 |
| CN | 101643501 | 2/2010 | |
| CN | 102653779 | 9/2012 | |
| EP | 2 474 558 | 7/2012 | |
| EP | 2 682 474 | 1/2014 | |
| WO | WO-2011/026447 | 3/2011 | |

OTHER PUBLICATIONS

Jakes et al., "Alteration of the pH-dependent Ion Selectivity of the Colicin E1 Channel by Site-directed Mutagenesis," J Biol Chem (1990) 265(12):6984-6991.
Qiu et al., "An engineered multidomain bactericidal peptide as a model for targeted antibiotics against specific bacteria," Nat Biotechnol (2003) 21:1480-1485.
Doherty et al., "A superior host strain for the over-expression of cloned genes using the T7 promoter based vectors," Nucleic Acids Research (1995) 23(11):2074-2075.
International Preliminary Report on Patentability for PCT/CN2012/085182, issued May 27, 2014, 9 pages.
International Search Report (including translation) for PCT/CN2012/085182, mailed Mar. 7, 2013, 12 pages.
Supplementary European Search Report for EP 12851604.4, issued Jun. 26, 2015, 8 pages.
Written Opinion (translation) for PCT/CN2012/085182, mailed Mar. 7, 2013, 11 pages.
Zinder and Boeke, "The filamentous phage (Ff) as vectors for recombinant DNA—a review," Gene (1982) 19:1-10.

* cited by examiner

*Primary Examiner* — Nancy Treptow
(74) *Attorney, Agent, or Firm* — Morrison & Foerster, LLP

(57) ABSTRACT

Provided are methods for highly expressing recombinant protein of engineering bacteria and the use thereof. The method comprises the following steps: (1) engineering bacteria of *Escherichia coli* with pET system are transfected with recombinant mutated plasmid to obtain positive monoclonal colonies; (2) the positive monoclonal colonies are enriched to obtain a seed bacteria solution, and the seed bacteria solution is induced to enrichment and growth in a large amount; and (3) the bacteria supernatant containing the recombinant protein as the expression target is separated, and then the recombinant protein in the bacteria supernatant is extracted and purified. The method is characterized in that the engineering bacteria of *Escherichia coli* with pET system are *E. coli* B834 (DE3). The components of the mass enrichment medium and the protein purification steps are also optimized such that a significant improvement in the yield and purity of the protein is achieved and the method is suitable for applying to the large-scale production of recombinant protein expressed by the engineering bacteria of *Escherichia coli*.

21 Claims, 1 Drawing Sheet

METHOD FOR HIGHLY EXPRESSING RECOMBINANT PROTEIN OF ENGINEERING BACTERIA AND USE THEREOF

CROSS-REFERENCE TO RELATED APPLICATION

This application is the national phase of PCT application PCT/CN2012/085182 having an international filing date of Nov. 23, 2012, which claims priority from Chinese patent application 201110380864.7, filed Nov. 25, 2011. The contents of these prior applications are incorporated herein by reference in their entireties.

TECHNICAL FIELD

The invention relates to biotechnology, especially to a method for highly expressing a recombinant protein of engineering bacteria and the use thereof.

BACKGROUND ART

In earlier studies, the inventor conducted creative experiments and invented/obtained a series of new recombinant peptides with colicin as attack point, which operationally connects a polypeptide (natural or artificial design) with identification and binding ability to target cells. For example, the new antibiotic PMC-AM1 disclosed in patent No. ZL200910092128.4, named "Novel Antibiotic Comprising an Antibody Mimetic, Its Preparation and Uses Thereof," shows a broad-spectrum antibiotic property and has stronger antibacterial activity on *Neisseria meningitidis*, Multidrug-resistance *Pseudomonas aeruginosa*, Vancomycin-resistant *Enterococcus faecalis* or Methicillin-resistant *Staphylococcus aureus* compared to the known antibiotics. The inventor's another invention entitled "A Novel Antibiotic, Its Nucleotide Sequence, Methods of Construction and Uses Thereof," with CN patent No. ZL200910157564.5, disclosed a series of new anti-*staphylococcus* antibiotics, such as PMC-SA1, PMC-SA2, PMC-SA3, PMC-SA4, PMC-SE as well as PMC-PA. In vivo and in vitro experiments, these antibiotics showed better targeting ability and stronger antibacterial activity than current antibiotics, antifungal antibiotic and chemotherapeutics drugs. Additionally compared with current antibiotics, these new antibiotics showed incomparable biological security and anti-drug-resistance characteristic.

The foresaid novel antibiotics as a whole are a kind of water-soluble proteins with 600 amino acid residues, but in which there is a hydrophobic domain with 40 amino acid residues near carboxyl terminal. Compared to preparation of other water-soluble proteins with one fold structure, there is more difficult in assembling and expressing of the novel antibiotics, which inevitably affects protein yield. It is necessary to improve current expression process to achieve high yield and priority of the novel antibiotics. It will make sense for bringing the novel antibiotics into actual clinical application and practice.

DISCLOSURE OF THE INVENTION

According to the peptide structure and characteristics of the new antibiotics disclosed in the current patent application, the present disclosure provides for a method for highly expressing recombinant protein of engineering bacteria.

In one aspect, the present disclosure provides for A method for highly expressing recombinant protein of engineering bacteria, wherein the end with hydrophilicity of the recombinant protein is colicin polypeptide and the other end with hydrophobic nature is polypeptide of target moiety which is capable of binding target, the method comprising:

(1) transfecting recombinant plasmid of expressing the recombinant protein into *E. coli* engineering bacteria with pET system to obtain positive monoclonal colonies, (2) producing seed bacteria solution of the positive monoclonal colonies, and inducing protein expression and enlargement culturing of the seed bacteria solution; the supernatant of the enlargement cultured solution contains expressed recombinant protein, (3) extracting and purifying the recombinant protein from the supernatant, wherein the *E. coli* engineering bacteria with pET system is *E. coli* B834 (DE3).

In some exemplary embodiments, the enlargement culturing medium used for said inducing enriching growth of the seed bacteria solution has water as solvent and comprises following components: NaCl 6.0-6.7 g/L, peptone 25.0 g/L, yeast powder 7.5 g/L, glucose 0.6-2.0 g/L, $Na_2HPO_4 \cdot 7H_2O$ 6.8-18.3 g/L, $KH_2PO_4$ 3.0-4.3 g/L, $NH_4Cl$ 1.0-1.4 g/L, $MgSO_4$ 0.2-0.4 g/L, $CaCl_2$ 0.01 g/L, methionine 0-40 mg/L.

In a preferable exemplary embodiment, said enlargement culturing medium has water as solvent and comprises following components: NaCl 6.0 g/L, peptone 25.0 g/L, yeast powder 7.5 g/L, glucose 2.0 g/L, $Na_2HPO_4 \cdot 7H_2O$ 6.8 g/L, $KH_2PO_4$ 3.0 g/L, $NH_4Cl$ 1.0 g/L, $MgSO_4$ 0.2 g/L, $CaCl_2$ 0.01 g/L, methionine 0-40 mg/L.

In some exemplary embodiments, said enlargement culturing of the seed bacteria solution comprises following steps: the seed bacteria liquid was added into a container and started growth for 2 to 3 hours at 30° C., when the OD value reached 0.4-0.6, the seed bacteria solution was conducted heat shock at 42° C. for 30 minutes, and then cooled down to 37° C. and kept growth for 1.5 to 2 hours before being collected.

In some exemplary embodiments, wherein in conducting heat shocks the IPTG with the final density 0.5 mmol/L was added into said enlargement-culturing medium.

In some exemplary embodiments, said extracting and purifying the recombinant protein from the supernatant was by CM ion exchange column, and the loading quantity of the supernatant depends on the ratio value which is 2.5 mg/ml between the weight of the recombinant protein in the supernatant and the volume of gel particles used in the CM ion exchange column.

In some exemplary embodiments, the eluent solution used for said extracting and purifying in CM ion exchange column is boric acid buffer solution with 0.2 mol/L NaCl.

In most exemplary embodiments, said recombinant plasmid of expressing the recombinant protein is selected from the group consisted of pBHC-SA1, pBHC-SA2, pBHC-SA3 pBHC-SA4, pBHC-SE, pBHC-PA and pBHC-PorA1.

In a further aspect, the present disclosure provides for the applications of any foresaid methods in preparing the recombinant peptides PMC-SA1, PMC-SA2, PMC-SA3, PMC-SA4, PMC-SE, PMC-PA or PMC-AM.

In another aspect, the present disclosure provides for a medium used for *E. coli* engineering bacteria with pET system, the medium has water as solvent and comprises following components: NaCl 6.0-6.7 g/L, peptone 25.0 g/L, yeast powder 7.5 g/L, glucose 0.6-2.0 g/L, $Na_2HPO_4 \cdot 7H_2O$ 6.8-18.3 g/L, $KH_2PO_4$ 3.0-4.3 g/L, $NH_4Cl$ 1.0-1.4 g/L, $MgSO_4$ 0.2-0.4 g/L, $CaCl_2$ 0.01 g/L, methionine 0-40 mg/L.

In some exemplary embodiments, said *E. coli* engineering bacteria with pET system is *E. coli* B834 (DE3), and the medium has water as solvent and comprises following components: NaCl 6.0 g/L, peptone 25.0 g/L, yeast powder 7.5 g/L, glucose 2.0 g/L, $Na_2HPO_4 \cdot 7H_2O$ 6.8 g/L, $KH_2PO_4$ 3.0 g/L, $NH_4Cl$ 1.0 g/L, $MgSO_4$ 0.2 g/L, $CaCl_2$ 0.01 g/L, methionine 0-40 mg/L.

The pET expression system provided by Novagen Company is a common system for cloning and expressing recombinant proteins in *Escherichia coli*. In this invention, a series of BL-21 (DE3) cells are transected with recombinant mutated plasmid disclosed in former patents and produced a higher protein expression yield than the TG1 cells does in this invention. By experimental data, we found that B834 (DE3), which is parent strain of BL-21 (DE3), has a more ideal expression productivity than BL-21 (DE3). The experimental data showed that the B834 (DE3) has dozens time of protein expression productivity than TG1 system does.

Medium is used for providing required carbon source, nitrogen source and inorganic salts for bacterium growth and multiplication. In present a medium with capability of improving the expression productivity of target protein is provided in present invention, which has an optimum formula for engineering bacteria fermentation. In this invention, the medium, named FB-M9 compound medium has an increased carbon source and nitrogen source and MgSO4, CaCl2 as well as some special amino acids that are required in growth of engineering bacteria with pET system. The medium moderately improved engineering bacteria reproduction speed and protein expression rate. And material cost of the improved medium is relatively low, which provides larger research space and higher development value for enlargement production in the future.

According to guide of the product manual, the carrying rate of CM ion gel particles used in purification system in this invention could not reach the ideal standard described in the product manual, which limits the recovery rate of target protein. In the present invention, the recovery rate has been significantly improved by the means of reducing loading quantity of sample while moderately increasing the gel volume, etc. The result also reflected that it is necessary to find or develop a kind of ion exchange gel with more efficient for large-scale industrial production of the target protein. In addition, the recombinant protein has fewer impurities owing to eluent with optimized concentration used in the ion exchange steps of this invention.

In summary, this invention provides a variety of optional more optimized method of expressing *E. coli* engineering bacteria recombinant proteins by the means of choosing engineering strains, optimizing the composition of medium, improving the purification and recovery rate, etc. This also provides a possible research direction and technical route for finally finding optimal procedure of high-efficiently expressing fusion protein needed. Compared with the original expressing system disclosed in former patents, the expressing system developed by present invention has improved the expressing production of fusion protein dozens of times, and provided a beneficial basis of theory and practice for the subsequent large-scale industrial production.

BRIEF DESCRIPTION OF THE DRAWINGS

FIG. 1a shows the elution process of protein with 150 ml CM gel column. FIG. 1b shows the elution process of protein with 600 ml CM gel column. The curve signified by two arrows in the figure represents the conductance value of the eluent. The area indicated by the arrows is a conductance peak caused by the loss of the sample PMC-SA in loading process. The area of the conductance peak caused by the loss of the sample PMC-SA reduced by 70% after increasing the volume of gel. Another curve: OD value of eluotropic protein.

DETAILED DESCRIPTION OF THE INVENTION

Figure 1:
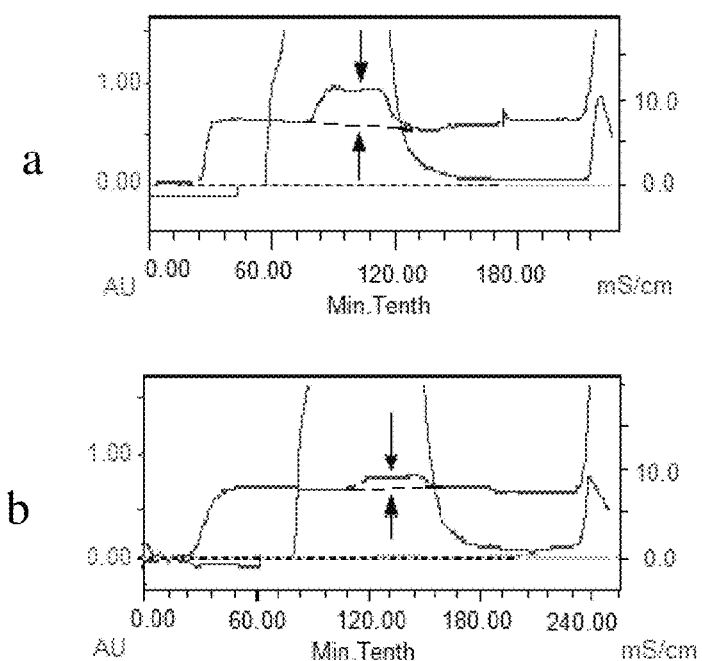
FIG. 1 shows the conductance value of eluent in the protein elution process with different volume gel column.

Following examples are just used for explaining the invention rather than limiting the scope of the invention.

The experimental equipment and instruments used in present invention as follows:

1. Bacterial Strain

*E. coli* TG1 engineering bacteria (AECOM, K. Jakes).

*E. coli* BL-21(DE3), B834(DE3), Nova Blue(DE3) and 618 engineering bacteria are all purchased from Novagen company.

*Staphylococcus aureus* ATCC BAA-42 is purchased from ATCC (American Type Culture Collection).

Plasmid: pBHC-SA1, pBHC-SA2, pBHC-SA3 pBHC-SA4, pBHC-SE, pBHC-PA, pBHC-PorA1. (These plasmids are recorded in patents ZL200910092128.4 and ZL200910157564.5, and preserved in the applicant's laboratory. The applicant promised to offer them to the public for necessary verification tests)

2. Main Reagents and Medicine

Yeast powder (OXIOD LP0021), peptone (OXIOD LP0042) as well another chemical reagent are all analytical reagent;

Dialysis bag Snake Skin Dialysis Tubing (Pierce, intercept molecular weight 1×104, Lot# KD32324):

Streptomycin Sulfate for injection (NCPC)

AMP ampicillin sodium for injection (Harbin pharmaceutical)

Anion exchange column gel (Pharmacia Biotech CM Sepharose™ Fast Flow Lot No. 225016).

LB liquid medium: Sodium chloride 1 g, peptone 1 g, and yeast 0.5 g were added into a 250 ml flask with the addition of 100 ml water, dissolved and autoclaved at 120° C. for 8 min LB solid medium:100 ml LB solid medium containing sodium chloride 0.5-1.5 g, peptone 0.5-2 g, yeast 0.3-1 g and agar 0.8-3 g. The LB solid medium is used for plate culture of single colony after strain recovery. Reagents were added into a 250 ml flask with the addition of 100 ml water, dissolved and autoclaved at 120° C. for 8 min FB-M9 complex medium: NaCl 6.0-6.7 g/L, peptone 25.0 g/L, yeast powder 7.5 g/L, glucose 0.6-2.0 g/L, Na$_2$HPO$_4$.7H2O 6.8-18.3 g/L, KH$_2$PO$_4$ 3.0-4.3 g/L, NH$_4$Cl 1.0-1.4 g/L, MgSO$_4$ 0.2-0.4 g/L, CaCl$_2$ 0.01 g/L, methionine 0-40 mg/L.

Improved FB-M9 complex medium: NaCl 6.0 g/L, peptone 25.0 g/L, yeast powder 7.5 g/L, glucose 2.0 g/L, Na$_2$HPO$_4$.7H$_2$O 6.8 g/L, KH$_2$PO$_4$ 3.0 g/L, NH$_4$Cl 1.0 g/L, MgSO$_4$ 0.2 g/L, CaCl$_2$ 0.01 g/L, methionine 0-40 mg/L. The methionine is 40 mg/L in the process with *E. coli* B834 (DE3) as engineering bacteria.

3. Key Instrument

Bio-Rad Protein chromatography purification system (BioLogic™ DuoFlow™ BioLogic™ Maximizer,™ BioLogic™ QuadTec™ UV-Vis Detector, BioLogic™ Econo™ Pump);

Ultrasonic Cell Disruptor (Soniprep 150), protein purification ion exchange column with 5 cm diameter (Pharmacia Biotech XK50), protein purification ion exchange column with 11 cm diameter (Shanghai Huamei);

Centrifuge (Beckman Coulter Avanti™ J-20XP, Beckman Coulter Avanti™ J-25);

Spectrophotometer (Bio-Rad SmartSpec™ Plus spectrophotometer);

Automatic fermenter (Bioengineering AG LP351-42L);

High pressure homogenizer (Italian NiroSoavi NS1001L2KSN 6564).

Statement: the biological materials adopted in this invention have been known before the application filing date and have been also preserved in this applicant's lab. The applicant promised to offer them to the public for necessary verification tests in the twenty years since application filing date.

Example 1

The Option Experiment of Engineering Bacterial Strains

Classic plasmid carried the colicin Ia and its immune protein gene (GenBank M13819) are from laboratory of Dr. Finkelstein. (Qiu, X. Q., et al. An engineered multi domain bactericidal peptide as a model for targeted antibiotics against specific bacteria. *Nat Biotechnol* (2003) 21:1480-1485). The classic plasmids were modified into following seven kinds of restructuring mutation plasmids in former researches: pBHC-SA1, pBHC-SA2, pBHC-SA3 pBHC-SA4, pBHC-SE, pBHC-PA, pBHC-PorA1.

Step 1. Transformation of Competent Cell

40 μL Novagen pET system engineering bacteria BL-21 (DE3), B834(DE3), Nova Blue(DE3), 618 were respectively transformed with 100 ng recombinant mutant plasmids pBHC-SA1, and then ice-incubated for 5 minutes, heat-shocked at 42° C. for 30 seconds, kept in ice for 2 minutes, added with 160 μl SOC medium and shake-cultivated at 220 rpm, 37° C. for 1 hour and then coated (LB medium with 1% agar and 50 ug/ml ampicillin, and cultured overnight at 37° C.). Single colonies are picked out and cultivated to obtain the seed strain, which is conserved at a low temperature.

Step 2: Strain Recovery

1. Preparing Recovered Bacteria Solution

The conserved strain was thawed at 4° C.; 1.5 ml of the strain is transferred into 10 ml LB medium (containing 50 μg/ml of AMP) and cultivated at 220 rpm, 37° C. for 5-8 hours.

2. Inoculation of Single Colony

The recovered bacteria solution was diluted $10^4$ or $10^5$ times; and 10 ul of the diluted bacteria solution was transferred on to LB solid medium plate (containing 50 μg/ml of AMP) and coated on the plate. The plate was placed in a humid box and cultivated in incubator at 37° C. for 10-12 hours till round single colonies have grown out on the surface of the medium.

Step 3. Enlargement Culturing the Single Colonies (1) Single colonies with regular round shape and smooth edge were picked up from the plate and respectively added into 1.5 ml LB medium, and cultivated at 220 rpm, 37° C. for 5-8 hours.

(2) Each 1.5 ml LB bacteria solution was transferred into a 100 ml LB medium, and cultivated at 220 rpm, 37° C. for 5-8 hours.

(3) Primary stage of enlargement culturing: the 100 ml of bacteria solution from the last step was added into 700 ml of improved FB-M9 complex medium and cultivated at 220 rpm, 37° C. for 5-8 hours.

(4) Secondary stage of enlargement culturing: 700 ml of bacteria solution from the primary stage is added into 6×700 ml of the improved FB-M9 complex medium and cultivated at 220 rpm, 37° C. for 5-8 hours.

(5) Third stage of enlargement culturing: 6×700 ml of bacteria solution from the secondary stage was added into 20 L of the improved FB-M9 complex medium and cultivated in a fermenter with stiffing rate of 220 rpm and maximum oxygen flow volume, 37° C. for 3-5 hours.

(6) Fermentation of engineered bacteria and induced expression of protein: 20 L of bacteria solution from the third stage of enlargement culturing was added into 200 L of improved FB-M9 complex medium and cultivated in a fermenter for induced expression of protein with stiffing rate of 220 rpm and maximum oxygen flow volume, at 30° C. for 2-4 hours; 42° C. for 0.5 hours; and 37° C. for 1-2 hours, note that IPTG is added at 42° C. with a final concentration of 0.5 mM.

Step 4. Collecting Bacteria by Centrifugation 6000 g fermentation liquor obtained from step 3 was centrifuged at 4° C. for 20 min. The precipitate was collected and added into 50 mM boric acid buffer (pH 9.0) for resuspend of the bacteria. Note: the boric acid buffer has 2 mM PMSF (phenylmethylsulfonyl fluoride serine protease inhibitor). All consequent steps after bacteria resuspend was conducted at 4° C.

Step 5. Cells Fragmentation

After suspension in pH 9.0 boric acid buffer completely, the bacteria cells was fragmented by a High Pressure Homogenizer at 500-600 bar for 7 times, with intervals of 3-5 minutes.

Step 6. Precipitation of the Bacteria DNA

The fragmented bacteria solution was centrifuged at 55000 g, 4° C. for 40 min. The supernatant was added with streptomycin sulfate (16 bottles of 1 million unit streptomycin sulfate were added into every 200 ml liquid supernatant), and stirred for 1 h with a magnetic stirrer.

Step 7. Dialysis

The bacteria solution from the step 6 was centrifuged at 55000 g, 4° C. for 20 min. The supernatant was placed into a dialysis bag and dialyzed for 8-12 hours in boric acid buffer, which was changed once every 4 hours.

Step 8. Purifying the Protein Medicine and Obtaining Antibacterial-Engineered Polypeptide The dialyzed bacteria solution was centrifuged at 55000 g, 4° C. for 20 min. The supernatant was measured the protein concentration in unit volume and placed into a Bunsen beaker for conducting protein purification by ion exchange method. The supernatant with known protein concentration was uploaded onto a CM ion exchange column. The sample loading and its ratio with the CM iron gel particular are according to the Product Manuals of CM ion exchange column. After being washed completely the CM ion exchange column was eluted with 50 mM boric acid buffer containing 0.3 M NaCl to obtain the novel antibacterial-engineered polypeptide.

The results are shown as Table 1, the expressing efficiency of PMC-SA by *E. coli* B834 (DE3) is the highest.

TABLE 1

| Expressing efficiency of different bacterial strain | | | | | |
|---|---|---|---|---|---|
| Engineering strain | TG1 | BL-21 | 618 | NavaBlue | B834 |
| Average unit production (mg/L) | 0.8 | 10 | 5.8 | 8.1 | 24.4 |

(Average unit production = Gross production of extracted PMC-SA1/volume of bacterial liquid)

The same operation was conducted on the other six restructuring mutation plasmids, the results appeared similar trend as the result listed in Table 1, namely, in contrast to other engineering bacteria, *E. coli* B834 (DE3) showed the highest expressing efficiency on all seven restructuring mutation plasmids.

The operation of heat shock as following adopted to inducing expression of protein in this embodiment was different from that in prior arts: After transferring the seed bacteria liquid into the tank, cultured the bacteria at an initial temperature 30° C. for 2 hours, when OD value had reached 0.4-0.6, conducted the heat shock at 42° C. for 30 minutes, then when the temperature low down to 37° C., cultured the bacteria again for 1.5 to 2 hours again. At this stage the OD value of bacteria liquid can reach to 1-3 or even more, and can be conducted collection. During this process, 0.5 mM IPTG was added to induce expression of pET engineering bacteria.

Before proposing present method, the usual process for preparing the recombinant peptides was as following:

100 ng of the mutant plasmids was ice-incubated with 40 μl competent cell of BL-21 engineered bacteria for 5 minutes, heat-shocked at 42° C. for 30 seconds, ice-incubated for 2 minutes, added with 160 μl of SOC medium, shake-cultivated at 220 rpm, 37° C. for 1 hour and then coated plate (LB medium with 1% agar and 50 μg/ml ampicillin, and cultured overnight at 37° C.). Single colonies were picked out for enlargement culturing.

Enlargement culturing: 8-10 L FB medium, 250 rpm, at 37° C. for 3-4 hours; was added with IPTG, 250 rpm, at 28° C. grew for 4 hours again; conducted centrifugation to precipitate bacteria at 4° C., 6000 g, 20 minutes. The precipitated bacteria was added with 80-100 ml 50 mM boric acid buffer (pH 9.0, 2 mM EDTA) kept at 4° C. to suspend, then added with 50 μg PMSF and broken by ultra sonication (4° C., 400 w, 1 minutes, repeat 4 to 5 times with intermittent 2-3 minutes for keeping the temperature of the liquid). Then the broken bacteria was conducted high-speed centrifugation (4° C., 75000 g, 90 minutes), the supernatant was added with 5 million units streptomycin sulfate to precipitate DNA (4° C. stirred for 1 hour), and 10000 g, 4° C., for 10 minutes centrifugation. The supernatant was put into dialysis bag with the molecular weight 15000 on 4° C., and dialyzed by 10 L 50 mM boric acid buffer overnight, then conducted centrifugation at 4° C., 10000 g, for 10 minutes once again. The supernatant was loaded on CM ion exchange column, after being flushed completely, eluted by 0.3 M NaCl+50 mM boric acid buffer, the new antibiotics can be obtained.

Example 2

Improving Medium

The classic FB medium for colicin Ia preparation (Qiu, X. Q., et al., "An engineered multi domain bactericidal peptide as a model for targeted antibiotics against specific bacteria," *Nat Biotechnol* (2003) 21:1480-1485; Jakes, K., et al., "Alteration of the pH-dependent Ion Selectivity of the Colicin E1 Channel by Site-directed Mutagenesis," *JBC* (1990) 265:6984-6991) has components as follows: peptone 25.0 g/L, yeast powder 7.5 g/L, NaCl 6.0 g/L and glucose 1.0 g/L.

In this invention, we adopted FB medium without glucose, the components of which as follows: peptone 25.0 g/L, yeast powder 7.5 g/L and NaCl 6.0 g/L. And the FB medium without glucose was configured with M9 medium at a special volume proportion to obtain the FB-M9 compound medium.

The mother liquor of M9 medium is 5×M9 and has components as follows: $Na_2HPO_4.7H_2O$ 64.0 g/L, $KH_2PO_4$ 15.0 g/L, $NH_4Cl$ 5.0 g/L, NaCl 2.5 g/L, $MgSO_4$ 1.5 g/L, $CaCl_2$ 0.05 g/L, and 2% glucose.

A preliminary attempt of the compound medium:

FB-M9: volume ratio between FB:M9 was 7:10, the components as follows: NaCl 6.7 g/L, peptone 25.0 g/L, yeast powder 7.5 g/L, $Na_2HPO_4.7H_2O$ 18.3 g/L, $KH_2PO_4$ 4.3 g/L, $NH_4Cl$ 1.4 g/L, $MgSO_4$ 0.4 g/L, $CaCl_2$ 0.01 g/L and glucose 0.6 g/L.

This invention adopted this formula for bacteria fermentation. The process was as step 3 in Example 1. The result shows in Table 2, wet bacteria weight got from per liter culture solution is significantly higher than that done through FB medium. The collected protein production is significantly improved with average production up to 30 mg/L.

TABLE 2

| Contrast of target protein production from test medium (PMC-SA1/BL-21 engineering bacteria) | | | |
|---|---|---|---|
| Fermenting in BF medium | | Fermenting in FB-M9 (7:10) medium | |
| Bacterial weight (g) | Protein contents (mg) | Bacterial weight (g) | Protein contents (mg) |
| 1 | 255.07 | 280.8 | 349.82 | 847.82 |
| 2 | 246.3 | 519.94 | 343.47 | 643.71 |
| 3 | 302.28 | 461.965 | 366 | 779.3 |
| 4 | 276.67 | 465.179 | 388.44 | 946.34 |
| AVG | 270.8 | 431.971 | 361.9325 | 804.2925 |

The final improved FB-M9 medium was obtained by further researches and repeated comparison in this invention. The production rate of the target protein can reach 34 mg/L as Table 3 shows, in the same fermentation conditions as Example 1.

The components of the improved FB-M9 medium as follows: NaCl 6.0 g/L, peptone 25.0 g/L, yeast powder 7.5 g/L, glucose 2.0 g/L, $Na_2HPO_4.7H_2O$ 6.8 g/L, $KH_2PO_4$ 3.0 g/L, $NH_4Cl$ 1.0 g/L, $MgSO_4$ 0.2 g/L and $CaCl_2$ 0.01 g/L. As the methionine was required in the growth of B834 engineering bacterium, in the process of B834 as engineering bacteria the methionine (40 mg/L) is added into the final improved FB-M9 medium.

TABLE 3

Comparison of improved FB-M9 medium with other medium on productivity

| | BL-21 | | | B834 | | |
|---|---|---|---|---|---|---|
| Engineering strains and the medium | | | | | | |
| | FB | FB-M9 (7:10) | Improved FB-M9 | FB | FB-M9 (7:10) | Improved FB-M9 |
| Average unit production (mg/L) | 10 | 24 | 25 | 22.3 | 30 | 34 |

Example 3

Optimizing Conditions for Purifying Protein

The basic structure of recombinant polypeptide (PMC-SA1, PMC-SA2, PMC-SA3, PMC-SA4, PMC-SE, PMC-PA, PMC-AM) prepared in this invention is Colicin Ia. The isoelectric point of colicin Ia is about 9.15, therefore the classic purification adopted is Ion Exchange Chromatography (Qiu, X. Q., et al., "An Engineered Multidomain Bactericidal Peptide as a Model for Targeted Antibiotics Against Specific Bacteria," *Nat Biotechnol* (2003) 21:1480-1485).

The principle is: In pH 9.0 boric acid buffer system, the majority of PMC-SA molecules exist as positive charge ions. When the CM gel particles with negative charge go through the chromatographic column, the recombinant protein molecules with positive charge was hung on the CM gel particles due to the electric charges attraction, while the other miscellaneous protein was rushed out of the gel column.

In this example, the other steps were as that in Example 1, but after the miscellaneous protein was rushed out completely, using boric acid buffer of 0.1 to 0.3 M NaCl gradiently to elute the gel column.

Owning to $Na^+$ ions having stronger positive property than the recombinant protein molecules, the recombinant protein was replaced from CM gel particles by $Na^+$ ion. There are two variables to be manipulated in the process of ion exchange and purification for a better protein yield: (1) NaCl with different concentration within 0.05-1 M can be chosen respectively to elute protein molecules with different positive charge mounted on CM gel particles. (2) The amount of CM gel particles adopted can be optimized: In the environment with certain ionic strength, the amount of protein carried by every CM gel particles is relatively constant. The volume of gel column is indispensable to be enlarged in order to increase the amount of protein carried by gel column.

CM Sepharose™ Fast Flow is anion exchange column gel produced by GE company. According to the manual, every 100 ml gel can combine with 9 mM cation. The actual usable combination capacity varies with the nature of sample in the process of dynamic combination, and molecular weight is inversely proportional with combined capacity. Its standard sample that has equivalent molecular weight with the recombinant peptides manufactured in this invention is Bovine COHb-(Mr69 kD), which has theoretically dynamic combined capacity 30 mg/ml. Namely, with 100 ml CM Sepharose™ Fast Flow glue to retrieve recombinant protein molecules, the theoretically highest recovery rate is about 300 mg (0.004 mM). But according to its manual operation, the actual dynamic combination capacity of recombinant protein molecules to CM gel particles reached only 3 mg/ml, just reached 10% of theoretical combined capacity.

In the experiment, we found that in the latter half process of washing out the miscellaneous protein, conductance curve will raise a small peak (as shown in FIG. 1a). According to this phenomenon, we speculate that when there is a large amount of recombinant protein in the sample, due to the limited capacity of CM gel particles with target protein, only a little part of the recombinant protein molecules can be recovered. The recombinant protein without being mounted on the CM gel particles has to be flushed out gel column together with miscellaneous protein. As the recombinant protein is positively charged, a short rising peak appears in the conductance curve.

In an optimized example of this invention: in order to reduce the loss of recombinant proteins, we reduced loading amount of sample to ⅓ of the manual regulation, and increased the volume of gel from 150 ml to 600 ml, namely the protein amount in the supernatant fluid: gel particle volume=2.5 mg/ml. The loss of the recombinant protein decreased in the process of elution. The experimental data showed that the recovery rate of recombinant proteins was increased 3.5 times; the results shown in FIG. 1b.

In addition, we set the gradient concentration of NaCl as 0.1 M-0.2 M-0.3 M in the boric acid buffer used in elution, and 0.2 M showed the highest eluting efficiency and protein purity, as shown in FIG. 2b.

Example 4

Detecting Protein Purity and Activity

Step 1. SDS-PAGE Electrophoresis

Figure 2:
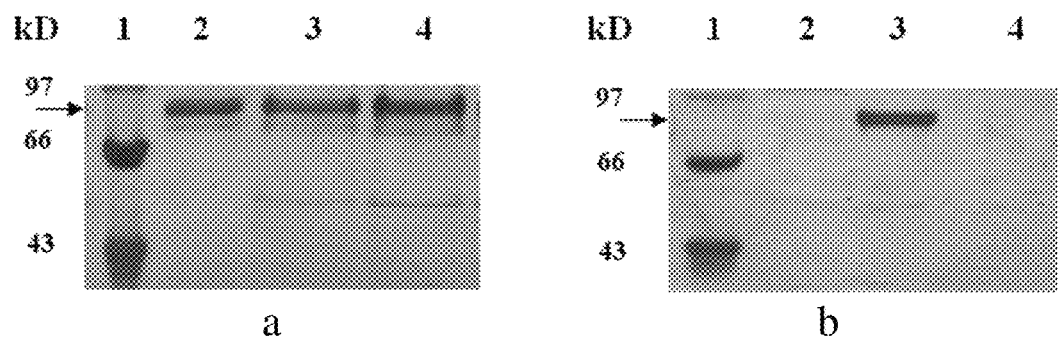
FIG. 2 shows SDS-PAGE Gel electrophoresis of the PMC-S. From left to right in the order: a. Marker, 2. PMC-SA1 produced by TG1, 3. PMC-SA1 produced by BL-21, 4. PMC-SA1 produced by B834; b. Marker, 2. PMC-SA1 eluted by boric acid buffer solution with 0.1 M NaCl, 3. PMC-SA1 eluted by boric acid buffer solution with 0.2 M NaCl, 4. PMC-SA1 eluted by boric acid buffer solution with 0.3 M NaCl.

The fusion protein samples obtained by optimized conditions of example 4 were conducted SDS-PAGE electrophoresis and silver nitrate dyeing. As shown in FIG. 2, there is a clear protein-imprinting stripe at the point of about 70 kD relative molecular weight, namely PMC-SA1 manufactured in this invention in the electrophoresis map a the map b shows the protein has eliminated mixed zone through the improved gradient elution in Example 4 and the purity is improved. The rest six kinds of recombinant proteins manufactured through the optimized method of this invention have also showed similar improved purification.

Step 2. Detecting the Antibacterial Activity

With the recombinant protein PMC-SA1 and PMC-AM that produced by the improved manufacturing method in the Examples 1, 2, 3, we conduct the following antibacterial activity test.

Figure 3:
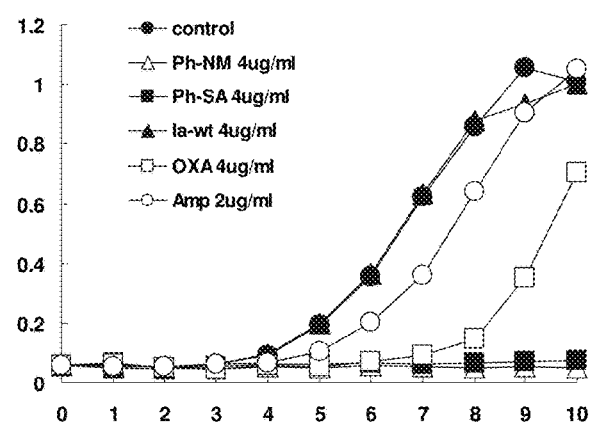
FIG. 3. Shows the inhibition curve of the PMC-SA against MRSA (BAA42). Y-axis represents light absorption value; X-axis represents bacterial growth time. Control: control group; Amp: ampicillin sodium; OXA: oxacillin; Ia-wt: wild type colicin Ia; PMC-SA1: anti-*staphylococcus aureus* polypeptide; PMC-AM: anti-*diplococcus meningitides* polypeptide.

The Methicillin-resistant *staphylococcus aureus* (MRSA, ATCC BAA-42) bacteria liquid 10 μl ($10^5$ CFU/ml) was inoculate into 10 ml BM medium and added with antimicrobial agents. According to the antimicrobial agents we set six parallel groups: ampicillin sodium 2 μg/ml, oxazocilline 4 μg/ml, wild type colicin Ia, PMC-SA and Ph-NM (4 μg/ml), and blank control group. Culturing at 37° C., 210 rpm, and testing optical density value per hour (595 nm), drawing the bacteriostasis curve, as shown in FIG. 3.

The bacteriostatic curve shows that the recombinant proteins produced by improved methods of this invention have good antibacterial activity.

The invention claimed is:

1. A method for expressing a recombinant polypeptide, the method comprising:
   (1) transfecting a recombinant plasmid capable of expressing a recombinant polypeptide into a recombinant bacteria to obtain a positive monoclonal bacterial colony comprising the recombinant plasmid,
wherein the recombinant polypeptide comprises a colicin portion at one end and a target-recognizing portion at the other end, and the colicin portion is hydrophilic and the target-recognizing portion is hydrophobic, and
wherein the bacteria is *E. coli* B834 (DE3) comprising a pET system,
(2) culturing the positive monoclonal bacterial colony in a culture medium to produce a seed bacteria culture of the positive monoclonal bacterial colony,
(3) culturing the seed bacteria culture in a growth medium to expand the bacteria culture,
(4) adding an inducer not present in the growth medium to induce the bacteria to express the recombinant polypeptide,
(5) collecting and breaking down the bacteria to obtain a supernatant containing the expressed recombinant polypeptide, and
(6) extracting and purifying the recombinant polypeptide from the supernatant,
wherein the growth medium comprises water, NaCl 6.0-6.7 g/L, peptone 25.0 g/L, yeast powder 7.5 g/L, glucose 0.6-2.0 g/L, $Na_2HPO_4 \cdot 7H_2O$ 6.8-18.3 g/L, $KH_2PO_4$ 3.0-4.3 g/L, $NH_4Cl$ 1.0-1.4 g/L, $MgSO_4$ 0.2-0.4 g/L, $CaCl_2$ 0.01 g/L, and methionine 0-40 mg/L.

2. The method of claim 1, wherein the growth medium comprises water, NaCl 6.0 g/L, peptone 25.0 g/L, yeast powder 7.5 g/L, glucose 2.0 g/L, $Na_2HPO_4 \cdot 7H_2O$ 6.8 g/L, $KH_2PO_4$ 3.0 g/L, $NH_4Cl$ 1.0 g/L, $MgSO_4$ 0.2 g/L, $CaCl_2$ 0.01 g/L, and methionine 0-40 mg/L.

3. The method of claim 1, wherein step (3) comprises the following steps:
culturing the seed bacteria culture for 2 to 3 hours at 30° C. until the OD value reaches 0.4-0.6, and
heat-shocking the expanded bacteria culture at 42° C. for 30 minutes wherein the heat-shocked bacteria culture is cooled down to 37° C. and cultured for 1.5 to 2 hours before being collected.

4. The method of claim 3, wherein the inducer is IPTG, and the IPTG with final concentration 0.5 mmol/L is added into the expanded bacteria culture in the heat-shocking step.

5. The method of claim 1, wherein the extracting and purifying step comprises loading a sample of the supernatant onto a CM ion exchange column such that the ratio between the weight of the recombinant polypeptide in the loaded sample of the supernatant and the volume of gel particles used in the CM ion exchange column is 2.5 mg/ml.

6. The method of claim 5, wherein the extracting and purifying step further comprises using for the CM ion exchange column an eluent solution which is a boric acid buffer solution with 0.2 mol/L NaCl.

7. The method of claim 1, wherein the recombinant plasmid is selected from the group consisting of pBHC-SA1, pBHC-SA2, pBHC-SA3, pBHC-SA4, pBHC-SE, pBHC-PA, and pBHC-PorA1.

8. The method of claim 1, wherein the recombinant polypeptide is selected from the group consisting of PMC-SA1, PMC-SA2, PMC-SA3, PMC-SA4, PMC-SE, PMC-PA, and PMC-AM.

9. A medium for culturing a recombinant *E. coli* bacteria comprising a pET system, the medium comprising water, NaCl 6.0-6.7 g/L, peptone 25.0 g/L, yeast powder 7.5 g/L, glucose 0.6-2.0 g/L, $Na_2HPO_4 \cdot 7H_2O$ 6.8-18.3 g/L, $KH_2PO_4$ 3.0-4.3 g/L, $NH_4Cl$ 1.0-1.4 g/L, $MgSO_4$ 0.2-0.4 g/L, $CaCl_2$ 0.01 g/L, and methionine 0-40 mg/L.

10. The medium of claim 9, wherein said recombinant *E. coli* bacteria comprising the pET system is *E. coli* B834 (DE3), and the medium comprises water, NaCl 6.0 g/L, peptone 25.0 g/L, yeast powder 7.5 g/L, glucose 2.0 g/L, $Na_2HPO_4 \cdot 7H_2O$ 6.8 g/L, $KH_2PO_4$ 3.0 g/L, $NH_4Cl$ 1.0 g/L, $MgSO_4$ 0.2 g/L, $CaCl_2$ 0.01 g/L, and methionine 0-40 mg/L.

11. The method of claim 1, wherein step (3) comprises the following steps:
culturing the seed bacteria culture for 2 to 3 hours at 30° C. until the OD value reaches 0.4-0.6, and heat-shocking the expanded bacteria culture at 42° C. for 30 minutes wherein the heat-shocked bacteria culture is cooled down to 37° C. and cultured for 1.5 to 2 hours before being collected.

12. The method of claim 2, wherein step (3) comprises the following steps:
culturing the seed bacteria culture for 2 to 3 hours at 30° C. until the OD value reaches 0.4-0.6, and heat-shocking the expanded bacteria culture at 42° C. for 30 minutes wherein the heat-shocked bacteria culture is cooled down to 37° C. and cultured for 1.5 to 2 hours before being collected.

13. The method of claim 1, wherein the recombinant polypeptide is selected from the group consisting of PMC-SA1, PMC-SA2, PMC-SA3, PMC-SA4, PMC-SE, PMC-PA, and PMC-AM.

14. The method of claim 2, wherein the recombinant polypeptide is selected from the group consisting of PMC-SA1, PMC-SA2, PMC-SA3, PMC-SA4, PMC-SE, PMC-PA, and PMC-AM.

15. The method of claim 3, wherein the recombinant polypeptide is selected from the group consisting of PMC-SA1, PMC-SA2, PMC-SA3, PMC-SA4, PMC-SE, PMC-PA, and PMC-AM.

16. The method of claim 4, wherein the recombinant polypeptide is selected from the group consisting of PMC-SA1, PMC-SA2, PMC-SA3, PMC-SA4, PMC-SE, PMC-PA, and PMC-AM.

17. The method of claim 5, wherein the recombinant polypeptide is selected from the group consisting of PMC-SA1, PMC-SA2, PMC-SA3, PMC-SA4, PMC-SE, PMC-PA, and PMC-AM.

18. The method of claim 6, wherein the recombinant polypeptide is selected from the group consisting of PMC-SA1, PMC-SA2, PMC-SA3, PMC-SA4, PMC-SE, PMC-PA, and PMC-AM.

19. The method of claim 7, wherein the recombinant polypeptide is selected from the group consisting of PMC-SA1, PMC-SA2, PMC-SA3, PMC-SA4, PMC-SE, PMC-PA, and PMC-AM.

20. The method of claim 11, wherein the recombinant polypeptide is selected from the group consisting of PMC-SA1, PMC-SA2, PMC-SA3, PMC-SA4, PMC-SE, PMC-PA, and PMC-AM.

21. The method of claim 12, wherein the recombinant polypeptide is selected from the group consisting of PMC-SA1, PMC-SA2, PMC-SA3, PMC-SA4, PMC-SE, PMC-PA, and PMC-AM.

* * * * *